(12) United States Patent
Miller et al.

(10) Patent No.: US 10,058,687 B2
(45) Date of Patent: Aug. 28, 2018

(54) APPLICATOR FOR APPLYING A LIQUID TO A LOCATION ON A BODY

(71) Applicant: Summit Medical, Inc., Eagan, MN (US)

(72) Inventors: Zachary W. Miller, Burnsville, MN (US); Kevin D. McIntosh, Brooklyn Park, MN (US); Daniel M. Broberg, Minnetonka, MN (US); Kevin Connelly, Chaska, MN (US)

(73) Assignee: Summit Medical, Inc., St. Paul, MN (US)

( * ) Notice: Subject to any disclaimer, the term of this patent is extended or adjusted under 35 U.S.C. 154(b) by 388 days.

(21) Appl. No.: 14/193,347

(22) Filed: Feb. 28, 2014

(65) Prior Publication Data

US 2014/0243756 A1 Aug. 28, 2014

Related U.S. Application Data

(60) Provisional application No. 61/770,431, filed on Feb. 28, 2013.

(51) Int. Cl.
*A61M 31/00* (2006.01)
*A61J 1/06* (2006.01)
*A61M 5/24* (2006.01)
*A61M 5/28* (2006.01)
*A61F 11/00* (2006.01)
*A61M 25/00* (2006.01)

(52) U.S. Cl.
CPC .............. *A61M 31/00* (2013.01); *A61J 1/067* (2013.01); *A61M 5/2425* (2013.01); *A61M 5/2455* (2013.01); *A61M 5/282* (2013.01); *A61M 5/285* (2013.01); *A61F 11/00* (2013.01); *A61M 25/0068* (2013.01); *A61M 2025/0081* (2013.01)

(58) Field of Classification Search
CPC . A61F 11/00; A61J 1/067; A61M 2025/0081; A61M 25/0068; A61M 31/00; A61M 5/2425; A61M 5/2455; A61M 5/282; A61M 5/285

See application file for complete search history.

(56) References Cited

U.S. PATENT DOCUMENTS 3,783,104 A * 1/1974 Henshilwood, Jr. ... C12M 23/32
600/572
3,918,435 A 11/1975 Beall et al.
(Continued)

FOREIGN PATENT DOCUMENTS

WO 2011079242 A2 6/2011

OTHER PUBLICATIONS

International Search Report and Written Opinion dated Jun. 5, 2014 for corresponding International Application No. PCT/US2014/019420, filed Feb. 28, 2014.

*Primary Examiner* — Imani Hayman
(74) *Attorney, Agent, or Firm* — Peter J. Ims; Westman, Champlin & Koehler, P.A.

(57) ABSTRACT

An applicator for administering a liquid to a selected location of a patient includes a main body having an interior cavity and a flexible outer wall. A frangible ampoule is configured to contain the liquid and configured to be positioned within the interior cavity of the main body. A hypodermic tube having a proximal end attached to the main body and a distal end. An applicator tip attached to the distal end of the hypodermic tube to dispense the liquid.

19 Claims, 6 Drawing Sheets

(56) References Cited

U.S. PATENT DOCUMENTS

| | | | | |
|---|---|---|---|---|
| 4,182,326 A | * | 1/1980 | Ogle | A61M 19/00 |
| | | | | 604/203 |
| 5,445,462 A | * | 8/1995 | Johnson | A61M 35/006 |
| | | | | 401/132 |
| 6,083,002 A | * | 7/2000 | Martin | A61C 3/005 |
| | | | | 433/89 |
| 6,238,120 B1 | * | 5/2001 | Mark | A45D 19/02 |
| | | | | 401/134 |
| 6,471,095 B1 | | 10/2002 | Cann | |
| 6,673,031 B2 | | 1/2004 | Mark | |
| 6,957,958 B2 | | 10/2005 | Rowe et al. | |
| 7,243,789 B2 | | 7/2007 | Discko, Jr. | |
| 7,866,907 B2 | | 1/2011 | Cable, Jr. et al. | |
| 2008/0298879 A1 | | 12/2008 | Chesak et al. | |
| 2011/0066172 A1 | | 3/2011 | Silverstein | |

* cited by examiner

APPLICATOR FOR APPLYING A LIQUID TO A LOCATION ON A BODY

CROSS REFERENCE TO RELATED APPLICATION(S)

This application claims the benefit of U.S. Provisional Patent Application Ser. No. 61/770,431 that was filed on Feb. 28, 2013, the contents of which are incorporated by reference in its entirety.

BACKGROUND

The discussion below is merely provided for general background information and is not intended to be used as an aid in determining the scope of the claimed subject matter.

The present disclosure relates to an applicator for use in applying a liquid to a selected location on a body of a living being. More particularly, the present disclosure relates to an applicator that can be utilized to control an amount of liquid that is applied within an ear canal of a living being, such as a human being.

Many young children and occasionally adults experience problems with their inner ears, which is typically caused by liquid pooling within the middle ear. The pooled liquid provides a growth medium for bacteria, which leads to ear infections that can cause severe pain. In order to keep liquid from building up within the middle ear, one option is to insert a vent tube into the tympanic membrane or eardrum that provides the necessary drainage to prevent the buildup of liquid and allow for drainage of the present liquid, and therefore, allowing the infection to resolve.

In order to be able to insert the vent tube through the ear canal, the tympanic membrane or eardrum is incised for the placement of the vent tube. To minimize the amount of discomfort and pain to the person having the vent tube insertion procedure, the tympanic membrane or eardrum is typically numbed prior to the incision where general anesthesia is otherwise not required. A typical numbing solution is phenol. As phenol is a dangerous compound, it is beneficial to control the amount and exposure to phenol to both the patient as well as the medical personnel.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

The present disclosure includes a storage and delivery device for delivering a dosage of a liquid, such as a numbing solution, to a location within a body of an animal, such as a human being. The storage and delivery device includes a main body having a continuous, flexible sidewall and a distal end cap sealingly attached to a bottom edge of the continuous sidewall. An inner surface of the continuous sidewall and the distal end cap define an interior cavity configured to accept a frangible ampoule that is configured and sized to contain the dosage of the liquid. With the ampoule positioned within the interior cavity, a top end cap is sealingly attached to the continuous sidewall proximate a top edge. The top end cap includes through bore that is in fluid communication with the interior cavity. A first end of a lumen or hypodermic tube is inserted into the through bore to create a seal between an outer surface of the lumen or hypodermic tube and the surface defining the through bore. An applicator tip is attached to a distal end of the lumen or hypodermic tube wherein the applicator tip controls the flow of the liquid to the location within the body.

The present disclosure includes a method of delivering a dosage of a liquid, such as a numbing solution, to a location on a body of an animal, such as an ear canal of a human being. The method includes positioning a frangible ampoule containing the liquid within an interior cavity of a main body having a continuous, flexible sidewall and end caps attached to opposing edges of the continuous sidewall. A proximal end of a hypodermic tube or lumen is secured through one of the end caps where an interior passage of the hypodermic tube or lumen is in fluid communication with the interior cavity. An applicator tip is optionally attached to a distal end of the hypodermic tube or lumen to control the application of the liquid to the location on the body. To deliver the dosage, an operator compresses the flexible, continuous sidewall until the sidewall engages the frangible ampoule. Additional manual force is applied through the sidewall to frangible ampoule to break the ampoule and release the liquid into the interior cavity. The device is then manipulated to locate the distal end of the hypodermic tube below the main body to create a liquid seal in at least the hypodermic tube. Applying pressure to the main body by compressing the sidewall causes the internal pressure within the interior cavity to rise and thereby force the liquid through the applicator tip to the location on the body, such as the tympanic membrane or eardrum.

DETAILED DESCRIPTION

Figure 1:
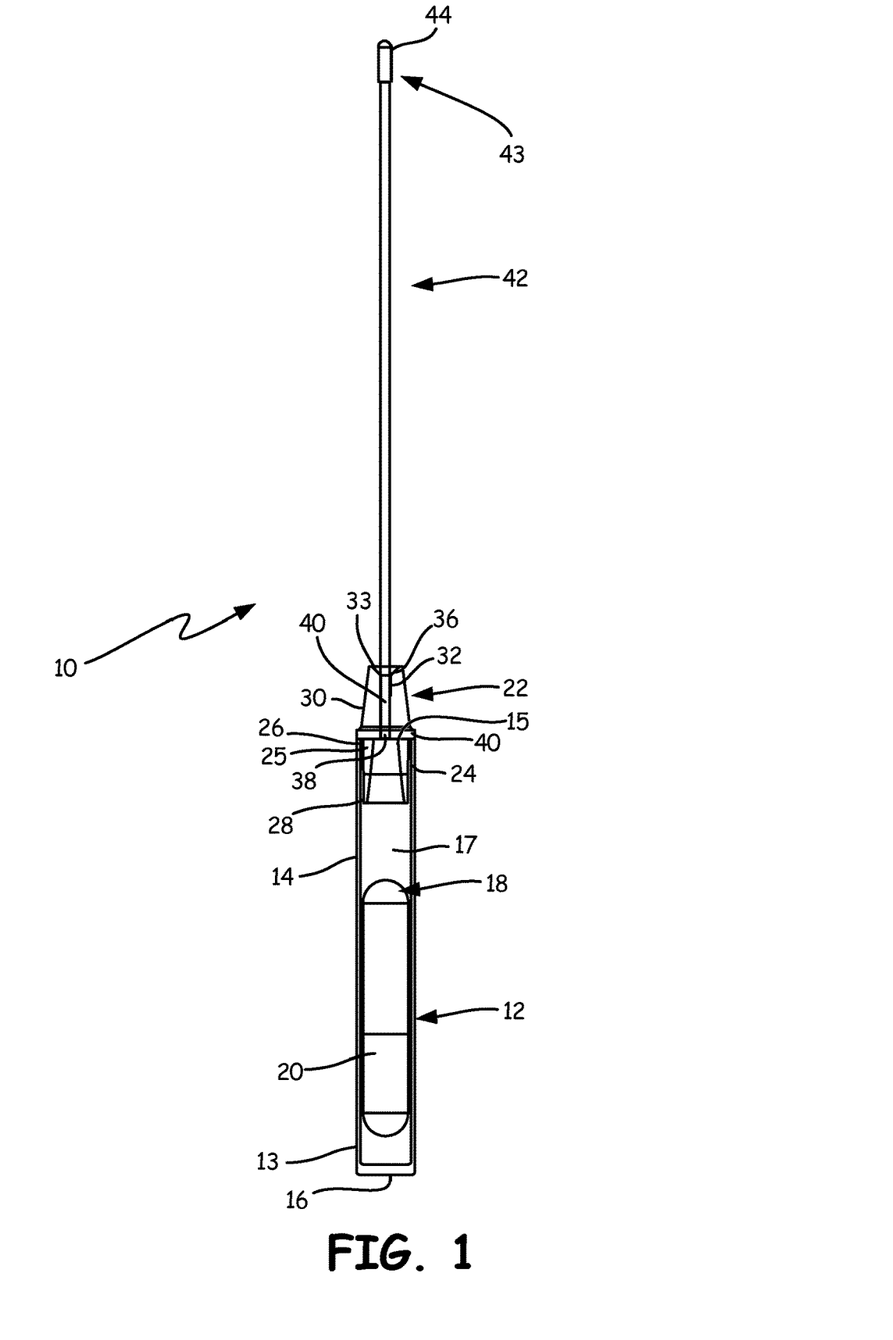
FIG. 1 is a schematic view of a liquid applicator for applying a liquid to the ear canal.

A storage and delivery device for delivering a dosage of a liquid to a selected location on a body of an animal, such as a human being, is generally illustrated at 10 in FIG. 1. While the device 10 can be utilized to deliver a dosage of different types of liquids to many locations on the body, the device 10 is configured to deliver a liquid within the ear canal of a patient. One such liquid is phenol, which is utilized to numb the tympanic membrane prior to making an incision for inserting a vent tube into the Eustachian tube.

The device includes a main body 12 having a substantially cylindrical sidewall 14. The substantially cylindrical sidewall 14 has a wall thickness that allows the sidewall 14 to flex when manual force is applied thereto. A bottom end cap 16 is sealingly connected to a bottom edge 13 of the sidewall 14. The sidewall 14 and the bottom end cap 16 define an interior cavity 17 that is of a sufficient size to receive an ampoule 18 filled with a selected amount of a liquid 20.

The sidewall 14 and the bottom end cap 16 are typically constructed as a unitary or monolithic member through a molding process. However, it is also contemplated that that bottom end cap 16 and the sidewall 14 be separate members that are sealingly connected together.

The sidewall 14 typically has a substantially circular cross-section. However, a sidewall 14 with a different cross-sectional configuration is also contemplated.

The sidewall 14 as illustrated is substantially flexible around a perimeter. However, it is also contemplated that portions of the sidewall 14 are rigid while other portions of the sidewall 14 are flexible along a length or around a perimeter of the sidewall.

A top end cap 22 has a bottom portion 24 that sealingly connects to the sidewall 14 proximate a top edge 15. The sealed connection prevents liquid from through the connection between the top edge 15 of the sidewall 14 and the top end cap 22. The bottom portion 24 has a substantially cylindrical configuration where the bottom portion 24 includes a sidewall 25 having a thickness that tapers from a top edge 26 to a bottom edge 28. The tapered thickness of the sidewall 25 allows the sidewall 25 to flex and conform to the inner surface of the sidewall 14 and thereby form a seal.

The bottom portion 24 is inserted into the interior cavity 17 until a shoulder 40 engages the top edge 15. When the shoulder 40 is proximate the top edge 15 of the sidewall 14, the bottom portion 24 forms a seal with the interior surface of the sidewall 14 and prevents the leakage of liquid there-between.

While a sidewall 25 in the bottom portion 24 with a tapered thickness is disclosed, other sealing mechanisms are also contemplated, including but not limited to a threaded engagement, a snap fit, a gasket, an o-ring, a sealant or an adhesive.

The top end cap 22 includes an upper portion 30 that includes a through bore 32 that is in fluid communication with the internal cavity 17. The through bore 32 has a top portion 34 that has a maximum diameter at a top edge 33 where the diameter gradually reduces to a main diameter at an intermediate location 36. The through bore 32 between the top edge 33 and the intermediate location 36 forms a funnel or frusto-conical configuration. The diameter of the through bore 32 is substantially consistent from the intermediate location 36 to a distal edge 38.

The funnel or frusto-conical configured portion of the through bore 32 between the top edge 33 and the intermediate location 6 guides a proximal end 40 of a lumen or hypodermic tube 42 into the through bore 32 between the intermediate location 36 and the distal edge 38. The proximal end 40 of the lumen or hypodermic tube 42 is located within the through bore 32 with an interference fit such that a seal is formed between the surface defining the through bore 32 between the intermediate location 36 and the distal edge 38 and the outer surface of the lumen or hypodermic tube 42. While an interference fit is contemplated, other securing mechanisms for connecting the proximal end 40 of the lumen or hypodermic tune 42 to the top end cap 22 are also contemplated including, but not limited to, an adhesive, a threaded engagement, a frictional connection caused by crimping the top end cap 22, a snap fit, a gasket, an o-ring and a sealant.

Figure 2A:
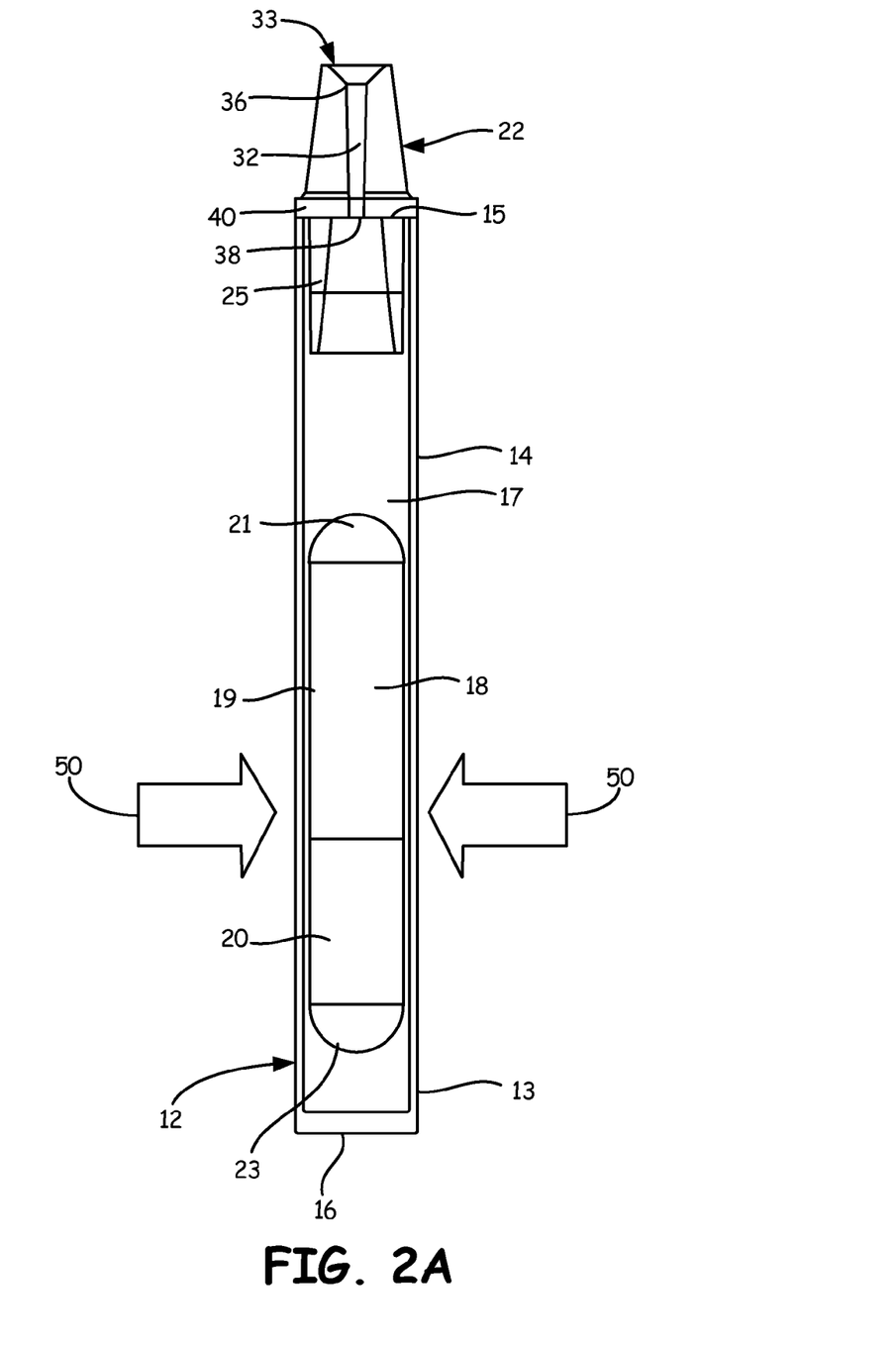
FIG. 2A is a schematic view of the main body of the applicator.
Figure 2B:
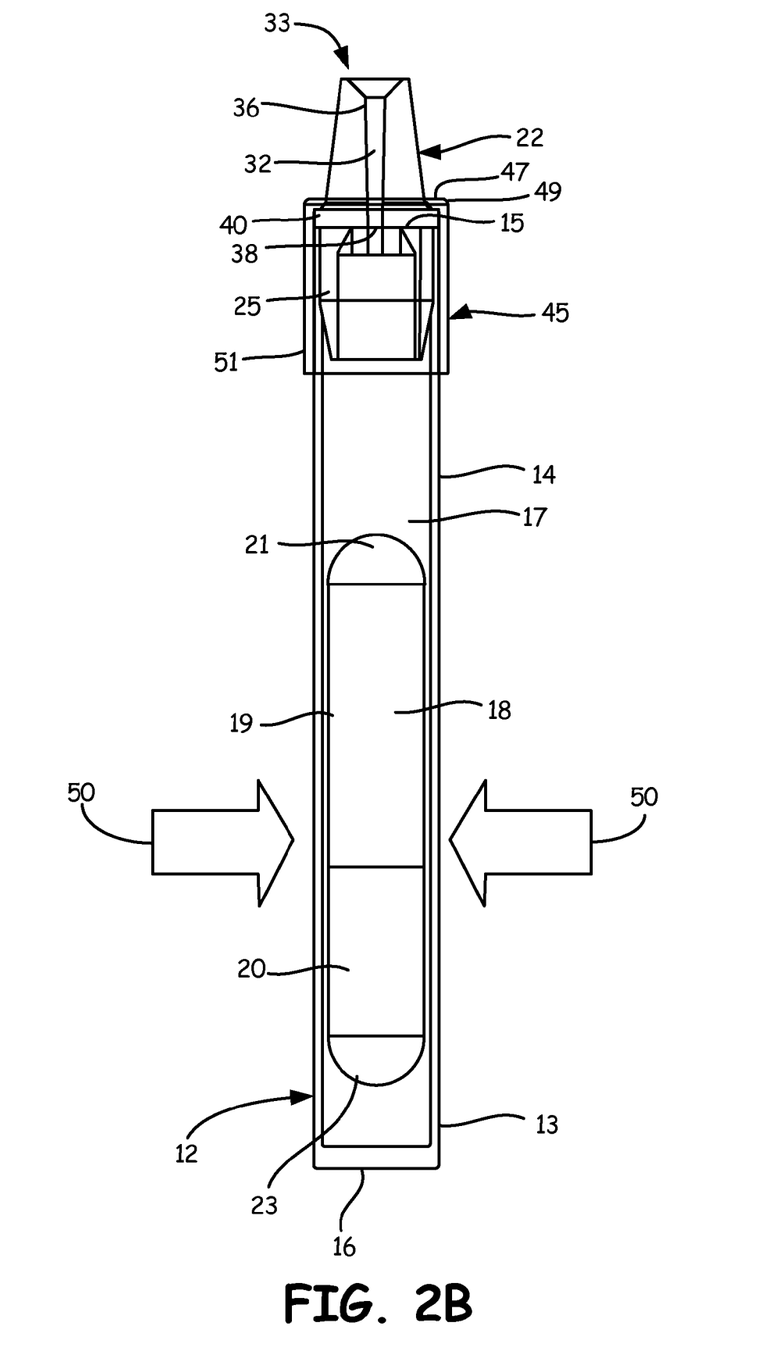
FIG. 2B is a schematic view of the liquid application with an end cover over the seam between the main body and the top end cap.

Referring to FIG. 2B, the device 10 can optionally include a proximal end cover 45. The proximal end cover 45 includes an aperture 47 through a top wall 49 that allows a continuous sidewall 51 extending from the perimeter of the top wall 49 to be positioned about the outer surface of the sidewall 14 of the main body 12. A diameter of the continuous sidewall 51 is less than a diameter of the sidewall 14 of the main body 12.

As the continuous sidewall 51 is positioned over the sidewall 14 of the main body 12, the outside diameter of the sidewall 14 is constricted. Constricting the outside diameter of the sidewall 14 causes an inner diameter of the sidewall 14 to constrict and better engage the sidewall 25 of the bottom portion 24 of the top end cap 22. The proximal end cover 45 therefore creates a more substantial seal between the sidewall 14 of the main body 12 and the sidewall 25 of the top end cap 22. While an interference fit between the proximal end cover 45 and the sidewall 14 is contemplated, other securing mechanisms are also contemplated included, but not limited to, a threaded engagement a clamp about the perimeter of the sidewall 14.

Figure 6:
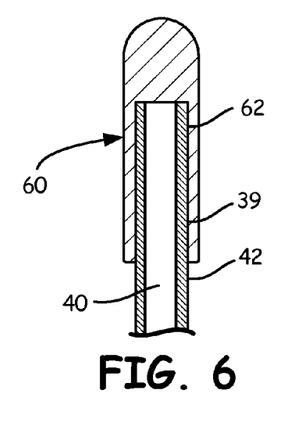
FIG. 6 is a sectional view of the applicator tip in FIG. 5.
Figure 7:
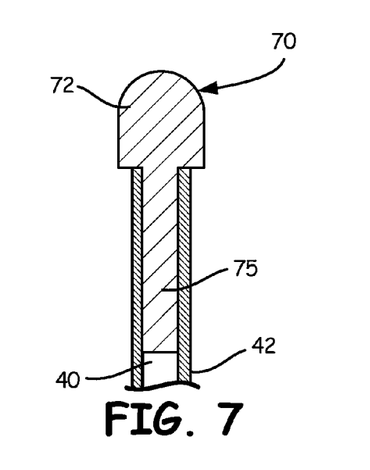
FIG. 7 is a sectional view wherein the applicator tip is attached to the interior surface of the lumen.

The lumen or hypodermic tube 42 includes an internal cavity 40 through which the liquid travels to a distal end 43 as best illustration FIGS. 6 and 7. An outer diameter of the lumen or hypodermic tube 42 is sized to fit within the ear canal of a human being. An applicator tip 44 is attached to the distal end 43 of the lumen or hypodermic tube 42.

Referring to FIGS. 1 and 2, a compressive force, typically manual force, as indicated by arrows 50, can be applied to opposing portions of the sidewall 14 of the main body 12 and cause the opposing portions to contact the frangible ampoule 18. Applying additional manual force to the opposing portions causes the ampoule 18 to break and thereby release the liquid, such as phenol. The sidewall 16 is typically transparent or translucent so that the personnel can see the location of the liquid within the main body 12.

The ampoule 18 is typically constructed from a glass material having a thin sidewall that allows the ampoule 18 to be easily broken. Alternatively, the ampoule 18 can be constructed of a polymeric material where the ampoule 18 has a manufactured weakness, such as a line with a thin wall thickness, that allows the ampoule 18 to be broken to release the liquid contained therein.

The ampoule 18 is configured with a cylindrical sidewall 19 and opposing end caps 21 and 23 such that the ampoule 18 is positionable within the interior cavity 17. However, other configurations of the ampoule 18 are also contemplated, provided the ampoule 18 is configured to be positioned within the internal cavity 17 of the main body 12.

Once the liquid has been released, the main body 12 is manipulated such that the lumen or hypodermic tube 42 is located below the main body 12 such that gravity causes the liquid to flow towards the top end cap 22 and into the through bore 40. With the liquid positioned within the through bore 40, a liquid seal is formed in the hypodermic tube or lumen 42 such that when additional pressure is placed upon the liquid by further compressing the sidewall 16 utilizing the compressive force as illustrated by arrows 50, the liquid is forced through the lumen or hypodermic tube 42 and the applicator tip 44 at the distal end 43 of the lumen or hypodermic tube 42.

A person administering the dose of the liquid, such as phenol, is able to contain the liquid within the interior cavity 17 and the lumen or hypodermic tube 42 and thereby prevent exposure to the liquid administering the dosage of the liquid. Further, the applicator 10 of the liquid can be utilized to administer the selected amount of the liquid through the applicator tip 44 by manipulating the pressure within the main body 12 which minimizes the exposure of the liquid to the patient.

The lumen or hypodermic tube 42 is preferably made of a flexible or bendable material that can be manipulated to a desired configuration to precisely position the applicator tip 44 in a selected location on the patient, such as proximate the tympanic membrane. The lumen or hypodermic tube 42 can be made of a metal such as stainless steel, a plastic or a combination of a plastic and a metal, as desired, to provide the necessary flexibility and rigidity to position the applicator tip 44 at the selected location.

The applicator tip 44 is typically made of a porous material such as a sponge, swab, wick or foam. The porous material allows the liquid to be dispensed through the tip 44. Referring to FIGS. 3-7, the tip can be attached in numerous ways and can also have many different configurations.

Figure 3:
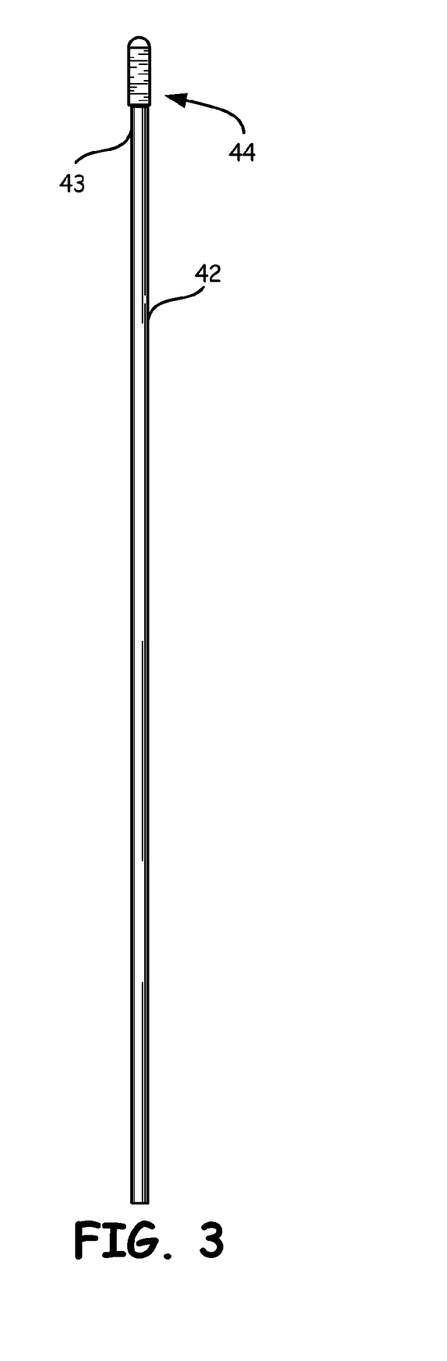
FIG. 3 is a view of the lumen or hypodermic tube having an applicator tip attached thereto.
Figure 4:
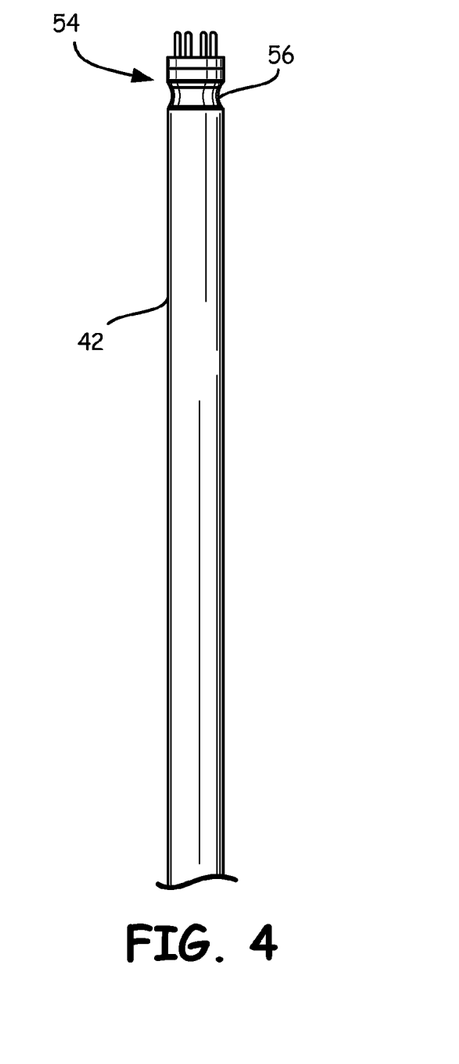
FIG. 4 illustrates the hypodermic tube with an alternative applicator tip.

Referring to FIG. 3, the applicator tip 44 is disclosed as being a foam material. Referring to FIG. 4, an applicator tip 54 can also be made of a solid porous material and can be retained to the hypodermic tube or lumen 42 utilizing a friction fit or interference fit as illustrated with a crimp 56 within the hypodermic tube or lumen 42.

Figure 5:
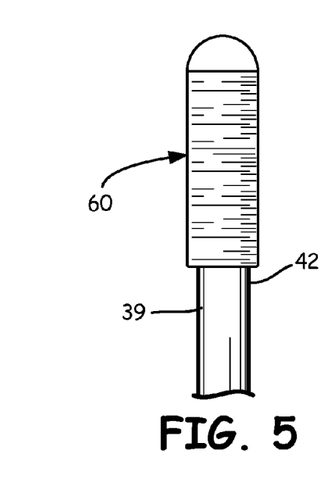
FIG. 5 is a front view of an applicator tip attached to the outside of the tube.

Referring to FIGS. 5 and 6, an applicator tip 60 is illustrated being attached to an outer surface 39 of the lumen or hypodermic tube 42. The attachment can also be through a friction fit or adhesive to the outer surface 39 of the lumen or hypodermic tube 42.

Referring to FIG. 6, the applicator tip 60 is shown to have an internal cavity 62 to which the outer surface 39 to the hypodermic tube 42 is attached.

Referring to FIG. 7, an applicator tip 70 can include a rounded upper portion 72 and a bottom, cylindrical portion 74 that is configured to fit within the lumen or the hypodermic tube 42 such that the applicator tip 70 can be retained with a friction fit or interference fit within the inside surface of the lumen or hypodermic tube 42. Alternatively a crimp in the outer surface of the lumen or hypodermic tube 42 can be utilized to provide additional retaining forces to retain the tip applicator tip 70 within the through bore of the lumen or hypodermic tube 42.

Figure 8:
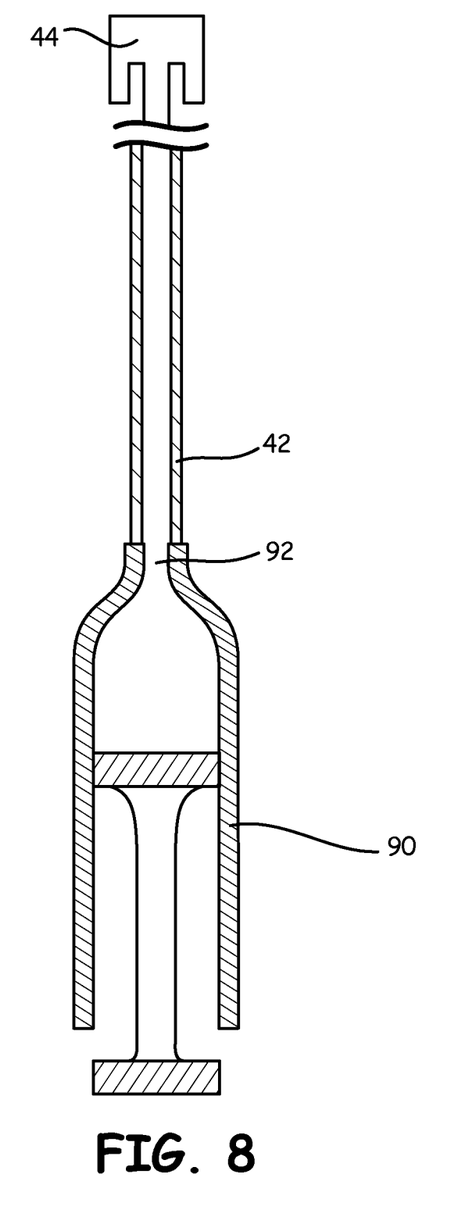
FIG. 8 is a schematic view of a syringe that can be utilized to control the dosage of phenol through the applicator tip.

Referring to FIG. 8, an alternative to the utilization to the main body 12 with the frangible ampoule 28 is illustrated. The alternative includes utilizing a syringe 90 that contains the liquid, such as phenol, where the syringe 90 then includes a lumen 92 to which the bendable hypodermic tube 42 is attached. It is contemplated that a threaded syringe 90 could be utilized to precisely control the amount of phenol that is force through the lumen 92, the hypodermic tube 42 and the applicator tip 44. However, other types of syringes may be utilized to obtain the same result of precisely delivering the desired amount of liquid, while minimizing the exposure of the liquid to the medical personnel as well as the patient.

Whether utilizing the main body 12 with the frangible ampoule 28 or the syringe 90 with the hypodermic tube 42 with the applicator tip 44, each embodiment is designed for a single use. After the single use, the applicator 10 or the syringe 90 and then is to be disposed.

Although the subject of this disclosure has been described with reference to several embodiments, workers skilled in the art will recognize that changes may be made in form and detail without departing from the spirit and scope of the disclosure. In addition, any feature disclosed with respect to one embodiment may be incorporated in another embodiment, and vice-versa.

What is claimed is:

1. An applicator for administering a liquid to a selected location of a patient, the applicator comprising:
    a main body having an interior cavity and a flexible outer wall;
    a frangible ampoule configured to contain the liquid and configured to be positioned within the interior cavity of the main body;
    a top end cap removably and sealingly attached to the flexible outer wall wherein a portion of the top end cap is positioned within the interior cavity;
    a proximal end cover positioned about the top end cap and having a continuous sidewall engaging with and constricting an outer surface of the flexible outer wall;
    a hypodermic tube having a proximal end attached to the top end cap and a distal end; and
    an applicator tip attached to the distal end of the hypodermic tube; and
    wherein a top end of the flexible outer wall has an outside diameter, and wherein the proximal end cover has an inside diameter that is less than the outside diameter.

2. The applicator of claim 1 and wherein the main body comprises:
    the flexible outer wall having a top edge and a bottom edge; and
    a bottom end cap attached to the flexible outer wall proximate the bottom edge.

3. The applicator of claim 2 and wherein the flexible outer wall and the bottom end cap are of a monolithic construction.

4. The applicator of claim 2 and wherein the top end cap comprises a through bore in fluid communication with the interior cavity.

5. The applicator of claim 4 and wherein the proximal end of the hypodermic tube is positioned within the through bore in the top end cap.

6. The applicator of claim 1 and wherein the frangible ampoule is constructed from a glass material.

7. The applicator of claim 1 and wherein the frangible ampoule is constructed of a polymeric material with a manufactured weakness.

8. The applicator of claim 1 and wherein the applicator tip comprises:
    a top portion that extends from the distal end of the hypodermic tube; and
    a bottom portion that engages the hypodermic tube.

9. The applicator of claim 8 and wherein the bottom portion comprises a cylindrical portion configured to be positioned within the hypodermic tube.

10. The applicator of claim 9 and wherein the bottom portion is retained within the hypodermic tube by crimping the hypodermic tube to create a friction fit.

11. The applicator of claim 9 and wherein the bottom portion is retained within the hypodermic tube with an interference fit.

12. The applicator of claim 9 and wherein the hypodermic tube is flexible.

13. An applicator for administering a liquid to a tympanic membrane of a human being, the applicator comprising:
    a main body having an interior cavity partially defined by a substantially cylindrical, flexible first sidewall having a bottom edge and a top edge;
    a top end cap configured to be positioned within the internal cavity proximate the top edge;

a proximal end cover having a second sidewall;

a frangible ampoule configured to contain the liquid and configured to be positioned within the interior cavity of the main body;

a flexible hypodermic tube having a proximal end attached to the main body and a distal end, wherein the tube is bendable into a selected configuration, the hypodermic tube being in fluid communication with the interior cavity such that the distal end can be manipulated to the selected configuration and positioned proximate the tympanic membrane to deliver the liquid thereto; and wherein a top end of the flexible outer wall has an outside diameter, and wherein the proximal end cover has an inside diameter that is less than the outside diameter such that a top portion of the flexible first wall constricts to form a seal with the top end cap.

14. The applicator of claim 13 and further comprising an applicator tip attached to the distal end of the hypodermic tube.

15. The applicator of claim 13 and wherein the main body comprises:
a bottom end cap attached to the flexible outer wall proximate the bottom edge.

16. The applicator of claim 15 and wherein the top end cap comprises a through bore in fluid communication with the interior cavity.

17. The applicator of claim 16 and wherein the proximal end of the hypodermic tube is positioned within the through bore in the top end cap.

18. The applicator of claim 13 and wherein the frangible ampoule is constructed from a glass material.

19. The applicator of claim 13 and wherein the frangible ampoule is constructed of a polymeric material with a manufactured weakness.

* * * * *